United States Patent [19]
Debourge et al.

[11] 3,948,942
[45] Apr. 6, 1976

[54] N-PHENYL MALEIC IMIDES

[75] Inventors: Jean-Claude Debourge, Lyon;
Jean-Michel Gaulliard, Orlienas;
Daniel Pillon, Lyon; Stephane Trinh,
Champagne, all of France

[73] Assignee: PEPRO, Societe pour le
Development et la Vente de
Specialities Chimiques, Lyon,
France

[22] Filed: Apr. 5, 1974

[21] Appl. No.: 458,098

[30] Foreign Application Priority Data
Apr. 18, 1973 France .............................. 73.15601

[52] U.S. Cl. ........................ 260/326.5 FM; 424/274
[51] Int. Cl.² .................................... C07D 207/404
[58] Field of Search ........................... 260/326.5 FM

[56] References Cited
UNITED STATES PATENTS

| 2,962,504 | 11/1960 | Walker et al. | 260/326.5 |
| 3,148,196 | 9/1964 | Ladd | 260/326.5 |
| 3,265,708 | 8/1966 | Stiteler | 260/326.5 |

Primary Examiner—Alton D. Rollins
Assistant Examiner—Mark L. Berch
Attorney, Agent, or Firm—McDougall, Hersh & Scott

[57] ABSTRACT

Fungicidal compositions, optionally contain chlorinated N- (2,4,6-trimethylphenyl)-maleic imides as active material. Such materials find use for controlling fungus disease in plants, especially in agriculture, viticulture, arboriculture, market-gardening and horticulture.

2 Claims, No Drawings

N-PHENYL MALEIC IMIDES

This invention relates to optionally chlorinated N-(2,4,6-trimethylphenyl)-maleic imides as new industrial products. The invention also relates to compositions suitable for use in controlling fungus disease in plants, especially in agriculture, viticulture, arboriculture, market-gardening and horticulture, containing as active material derivatives corresponding to the general formula:

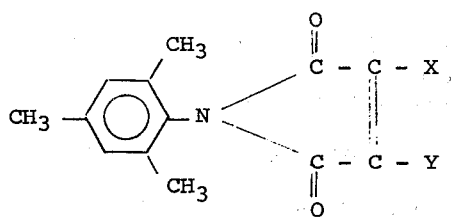

in which X and Y, which may be the same or different, represent hydrogen or a halogen atom.

Numerous N-phenyl maleic imides substituted on the phenyl nucleus are already known. In particular, Torgeson, Hensley and Lambrecht, Contributions from Boyce Thompson Institute, vol. 22, pages 67 to 70, have shown that N-(2,4-dimethylphenyl)-maleic imides and chloromaleic imides, and above all their 2,6-dimethylated homologues, are active against Pythium.

The compounds according to the invention have been found to show better fungicidal properties with respect to ground fungi and, generally, a wider spectrum than similar known compounds.

The compounds according to the invention can be prepared by processes known per se. In one process, optionally halogenated maleic anhydride is condensed with 2,4,6-trimethylaniline at a temperature around 180° C. In the case of chloromaleic imides, direct condensation can also be carried out in an acetic medium at temperatures around 100°C. It is also possible to apply a two-stage process, in which the two aforementioned reactants are first condensed at ambient temperature in an aromatic solvent, especially benzene, to form an N-(2,4,6-trimethylphenyl)-maleimic acid which is then cyclized by dehydration at boiling point with acetic anhydride in the presence of traces of sodium acetate.

It has been possible, by this particular process, to obtain N-(2,4,6-trimethylphenyl)-maleic imide and N-(2,4,6-trimethylphenyl)-chloromaleic imide, hereinafter referred to as compounds 1 and 2, respectively, whilst N-(2,4,6-trimethyl-phenyl)-dichloromaleic imide (compound 3) has been obtained by the second process.

The known compounds, N-(2,4-dimethylphenyl)-maleic imide (A) and N-(2,6-dimethylphenyl)-maleic imide (B), were also prepared for comparison. The preparation and fungicidal properties of the compounds according to the invention are illustrated in, but by no means limited to, the following Examples.

EXAMPLE 1 a. Preparation of N-(2,4,6-trimethylphenyl)-maleimic acid 27 g (0.2 mole) of 2,4,6-trimethylaniline and a solution of 19.6 g (0.2 mole) of maleic anhydride in 200 ml of benzene are mixed. The reaction is carried out with stirring for 1 hour at room temperature. The N-(2,4,6-trimethylphenyl)-maleimic acid precipitates, is filtered and then dried. The acid with a boiling point of 152° to 153°C is obtained in a yield of 97% after recrystallization from ethanol.

b. Preparation of N-(2,4,6-trimethylphenyl)-maleic imide

A mixture of 30.3 g (0.13 mole) of the N-(2,4,6-trimethylphenyl)-maleimic acid obtained as described above, 180 ml of acetic anhydride and 0.65 g of sodium acetate, is heated to reflux for 1 hour. After cooling, the mixture is poured into 500 ml of water with vigorous stirring. The imide precipitates, being washed with water, dried and recrystallized from 100 ml of ethanol.

| Melting point: | 100°C |
|---|---|
| Yield: | 84 % |

Centesimal analysis for $C_{13}H_{13}NO_2$

| % | C | H | N |
|---|---|---|---|
| Calculated | 72.56 | 6.05 | 6.51 |
| Found | 72.64 | 6.06 | 6.54 |

EXAMPLE 2

Preparation of N-(2,4,6-trimethylphenyl)-chloromaleic imide

The procedure is as in Example 1 using a mixture of 27 g (0.2 mole) of 2,4,6-trimethylaniline and a solution of 26.5 g (0.2 mole) of chloromaleic anhydride in 200 ml of benzene. The intermediate acid is cyclized to form the maleic imide in question.

| Melting point: | 103°C |
|---|---|
| Yield: | 76 % |

Centesimal analysis for $C_{13}H_{12}NO_2Cl$

| % | C | H | N | Cl |
|---|---|---|---|---|
| Calculated | 62.53 | 4.81 | 5.81 | 14.23 |
| Found | 62.68 | 4.86 | 5.70 | 14.19 |

EXAMPLE 3

Preparation of N-(2,4,6-trimethylphenyl)-dichloromaleic imide 4.4 g (0.03 mole) of 2,4,6-trimethylaniline are added dropwise to a solution of 5 g (0.03 mole) of 2,3-dichloromaleimic anhydride in 15 ml of glacial acetic acid. A precipitate is formed, dissolving in the reaction medium under heat. This medium is kept at 100°C for 1 hour. Dilution of the reaction medium with 100 ml of water gives a precipitate which is washed and then recrystallized from a mixture of water and ethanol (⅓ : ⅔).

| Melting point: | 123°C |
|---|---|
| Yield: | 86 % |

Centesimal analysis for $C_{13}H_{11}NO_2Cl_2$

|  | C | H | N | Cl |
|---|---|---|---|---|
| Calculated | 54.93 | 3.87 | 4.93 | 25.0 |
| Found | 55.06 | 3.98 | 5.03 | 24.90 |

EXAMPLE 4

In vitro spore germination test

The compounds, according to the invention, are tested for their effect on the germination of spores of the following fungi:

*Alternaria solani*, responsible for alternariosis,
*Botrytis cinerea*, responsible for grey rot,
*Monilia fructigena*, responsible for moniliosis,
*Piricularia oryzae*, responsible for piriculariosis in rice,
*Uromyces appendiculatus*, responsible for bean rot.

Each test is carried out as follows: a solution of 0.1 g/l of the material to be tested, in acetone, is sprayed onto plates of glass. An aqueous suspension containing approximately 80,000 spores/cc of the fungus is applied following evaporation of the acetone.

If the material to be tested is insoluble in acetone, a mixture of one part by volume of the aforementioned aqueous suspension and one part by volume of an aqueous suspension, containing 0.1 g/l of the material to be tested, of a wettable powder with the following composition is applied to the plates of glass:

| active material to be tested | 20 % |
|---|---|
| deflocculant (calcium lignosulphate) | 5 % |
| wetting agent (sodium alkylaryl sulphonate) | 1 % |
| filler (aluminum silicate) | 74 % |

This wettable powder is then mixed with a quantity of water calculated for one application in the required dose.

This is followed by incubation for 24 hours at 20°C in an atmosphere of 100 % relative humidity.

The number of spores that have germinated is then checked, being expressed as percentage germination in relation to an untreated control.

Under these conditions, products 1 to 3 completely inhibit germination of all the fungi used in this test in a dose of 0.05 g/l.

EXAMPLE 5

In vitro mycelian growth test

Each test is carried out as follows:

A suspension in gelose (agar-agar), containing approximately 70,000 spores/cc of the fungus, is poured into a Petri dish at a temperature around 50°C. This suspension is left to harden, after which discs of filter paper impregnated with a suspension of the material to be tested in various concentrations are placed on it. The material to be tested is in the form of a wettable powder prepared in the same way as described in Example 4.

A Petri dish containing discs impregnated with distilled water is used as control.

Under these conditions, compounds 1 to 3 completely inhibit *Pythium de Baryanum*, responsible for damping off of seedlings, and *Rhizoctonia solani*, responsible for canker of the neck, in a dose of 0.25 g/l. In a dose of 0.01 g/l, the compound still effectively inhibits *Pythium de Baryanum*, whilst compounds A and B produce only poor to moderate inhibition. In a dose of 0.1 g/l, compound No. 1 is also completely effective against

*Fusarium oxysporum*, responsible for tracheomyosis,
*Sclerotinia sclerotiorum*, responsible for sclerotiniosis,
*Verticillium dalhiae*, responsible for verticilliosis,
*Cercosporella heotrichoides*, responsible for root rot,
*Helminthosporium*, responsible for helminthosporiosis,
*Septoria nodorum*, responsible for septoriosis in cereal crops,
*Fusarium nivale*, responsible for fusariosis in cereal crops,
*Fusarium roseum*, responsible for fusariosis in cereal crops,
*Cercospora beticola*, responsible for cercosporiosis.

It should be noted that, in the case of this latter fungus, compound No. 1 produces effective inhibition in a dose of 0.01 g/l, whilst the action of compounds A and B, used in the same dose, is distinctly inadequate.

EXAMPLE 6

In vivo plant test

The compounds according to the invention are studied for their effect on the following fungi:

*Septoria apii*, responsible for septoriosis in celery,
*Phytophthora solani*, responsible for tomato mildew in tomato plants (Marmande variety),
*Alternaria solani*, responsible for alternariosis,
*Uromyces appendiculatus*, responsible for bean rot,
*Plasmopara viticola*, responsible for vine mildew.

Pot-grown bean, celery, tomato and vine plants are treated by spraying onto the underneath of the leaves, with a spray gun, an aqueous suspension of a wettable powder of the kind described in Example 4, in the required dilution, containing the active material to be tested in the dose in question. Each test is repeated twice.

After 24 hours, the plants are infected by spraying an aqueous suspension of approximately 80,000 spores/cc of the fungus selected onto the underneath of the leaves.

The pots are then kept in an incubation cell for 48 hours at 20°C/100 % relative humidity.

The plants are checked 15 days after infestation.

Under these conditions, the following results are obtained:

Compound No. 1 affords excellent protection against *Septoria apil* in a dose of 0.25 g/l;

Compounds 1 and 2 afford good protection against *Alternaria solani* in a dose of 0.5 g/l;

Compound No. 1 affords good protection against *Phytophthora solani* in the same dose, whilst the known compounds A and B are inactive or substantially inactive;

Compound No. 1 affords good protection against *Uromyces appendiculatus* in a dose of 0.5 g/l, whilst compounds A and B are ineffectual;

Compounds 1 and 2 afford excellent protection against *Plasmopara viticola* in a dose of 0.25 g/l, whilst compounds A and B afford good protection in the same dose. In half the dose, Compound No. 2 still affords excellent protection and Compound 1 good protection, whilst compounds A and B are completely ineffectual.

These tests also demonstrate the complete absence of phytotoxicity of Compound No. 1 with respect to tomato, bean, vine and celery plants.

EXAMPLE 7

In vivo ground fungi test

The compounds according to the invention are tested for their action on:

Pythium de Baryanum in cucumbers,
Fusarium oxysporum in melons,
Rhizoctonia solani in cotton.

Each test is carried out as follows:

A medium containing a culture of the fungus is mixed with sterilized soil, and pots filled with the resulting mixture. The soil is infested after 8 days. It is then treated by sprinkling with a suspension of the material to be tested in various concentrations. The material to be tested is in the form of a wettable powder prepared in the same way as described in Example 4.

Cucumber, melon and cotton seeds are then sown in the treated soils.

The results are assessed 15 days after sowing by counting the number of destroyed or diseased plants in relation to an untreated control and an uncontaminated control.

Under these conditions, the following results are obtained:

Compound No. 1 affords complete protection against *Fusarium oxysporum* in a dose of 0.25 g/l, whilst compounds A and B afford only poor protection;

Compounds 1, 2 and 3 afford complete protection against *Rhizoctonia solani* in a dose of 2 g/l, whilst compounds A and B are ineffectual in the same dose;

Compound No. 1 affords complete protection against *Pythium de Baryanum* in doses upwards of 0.15 g/l, whilst compounds A and B afford only moderate protection in the same dose.

EXAMPLE 8

Open-air test on septoriosis of wheat

Tender winter wheat seeds, previously contaminated to 60–70% with *Septoria nodorum*, are powder-coated with the following composition:

| | |
|---|---|
| Active material to be tested | 21% by weight |
| Wetting agent (sodium alkylarylsulphonate) | 1% |
| Filler (aluminium silicate) | 78% |

The treated seeds and the untreated seeds, serving as control, are sown to a depth of 1 cm in trays filled with moist sand, after which the trays together with the seeds are placed in a cold frame regulated to 4°C/90% humidity.

After 6 weeks, the results are assessed by counting the number of seedlings showing the patches of ocellus characteristic of septoriosis. The seedlings are also inspected for any signs of phytotoxicity.

Under these conditions, Compound 1, used in a dose of 100 g m.a./cwt., affords excellent protection comparable to the protection obtained with benomyl in a dose of 60 g m.a./cwt. In addition, there are no signs of phtotoxicity.

EXAMPLE 9

Open-air test on helminthosporiosis in barley

Winter barley seeds (Ager variety) are treated by dry powder coating with the composition containing the material to be tested, and are then sown in 1.5 m$^2$ plots at the end of November. When vegetation begins in spring, the controls show clear signs of helminthosporiosis recognizable from the long yellow or brown streaks on their leaves.

This inspection is made during earing in the month of May by pulling up all the stalks and counting the number of sick stalks and healthy stalks. Untreated plants and plants treated with a mercuric compound are used for control and reference purposes.

Under these conditions, Compound No. 1 is found to afford complete protection to the plants (less than 0.5% of sick plants) in a dose upwards of 25 g/cwt., and is therefore comparable in its effect with the mercuric compound used as reference.

Similar tests with manebe on the Ager variety show that Compound No. 1 affords better protection in a dose of 50 g/cwt. than manebe in a dose of 160 g/cwt.

In all these tests, there were no signs of phytoloxicity on the plants whose seeds had been treated with the compound according to the invention.

These results clearly demonstrate the versatility of the compounds according to the invention in regard to their fungicidal properties, with the results that these compounds can be used to control both phycomyceteae, in particular vine, tomato and potato mildew; numerous ground fungi; seed parasites (fusariosis, helminthosporiosis); fungi causing disease in the aboveground part of plants, such as alternariosis, wilting rot and septoriosis, and disease affecting coffee trees, such as antrachnosis and rot.

Finally, tests have shown that Compound No. 1 is more effective than the captafol used as reference against antrachnosis (*Colletotrichum coffeanum*) and rot (*Hemileia vastatrix*) in coffee trees.

This remarkable range of properties is all the more surprising insofar as these properties cover a wider range than and, at the same time, are superior to those of similar known compounds.

By virtue of these properties, the compounds according to the invention can be used on a preventive or curative basis for protecting plants against fungus disease, especially in agriculture, arboriculture, horticulture, market-gardening and viticulture, and for treating seeds, stored produce and materials both during storage and in use.

In practice, the doses in which the compounds according to the invention are used can vary within wide limits, depending upon the virulence of the fungus to be controlled and the climatic conditions.

Generally, doses of from 0.01 to 5 g/l of active material are adequate.

In practice, the compounds according to the invention are rarely used on their own. More often they are an integral part of formulations which generally comprise a support and/or a surfactant in addition to the active material according to the invention.

In the context of the invention, a support is an organic or mineral, natural or synthetic material with which the active material is associated to facilitate its application to the plant, to seeds or to soil, or its transportation or handling. The support can be solid (clays, natural or synthetic silicates, resins, waxes, solid fertilizers) or fluid (water, alcohols, ketones, petroleum fractions, chlorinated hydrocarbons, liquefied gases).

The surfactant can be an ionic or non-ionic emulsifier, dispersant or wetting agent such as, for example, salts of polyacrylic acids and lignin-sulphonic acids, condensates of ethylene oxide with fatty alcohols, fatty acids or fatty amines.

The compositions according to the invention can be prepared in the form of wettable powders, powders for dusting, granulates, solutions, emulsifiable concentrates, emulsions, suspended concentrates and aerosols.

The wettable powders according to the invention can be prepared in such a way that they contain from 20 to 95% by weight of active material, and they normally contain, in addition to a solid support, from 0 to 5% of a wetting agent, from 3 to 10% by weight of a dispersant and, when necessary, from 0 to 10% by weight of one or more stabilizers and/or other additives, such as penetration agents, adhesives and antilumping agents, colorants, etc.

One example of the composition of a wettable powder is given below, the percentages being expressed in weight:

| | |
|---|---|
| Active material | 50 % |
| Calcium lignosulphate (deflucculant) | 5 % |
| Isopropylnaphthalene sulphonate (wetting agent) | 1 % |
| Anti-lumping silica | 5 % |
| Filler (kaolin) | 39 % |

The powders for treating seeds are normally prepared in the form of a dust-like concentrate similar in composition to a wettable powder, but without any dispersant. They can be diluted in situ with a complementary quantity of fluid support to give a composition which can be conveniently used for coating the seeds to be treated.

One example of the composition of a powder for treating seeds is given below:

| | |
|---|---|
| Active material | 50 % |
| Anionic wetting agent | 1 % |
| Anti-lumping silica | 6 % |
| Kaolin (filler) | 43 % |

Aqueous dispersions and emulsions, for example compositions obtained by diluting with water a wettable powder or an emulsifiable concentrate according to the invention, are included within the general scope of the invention. These emulsions can be of the water-in-oil type or of the oil-in-water type, and can have a thick consistency resembling that of a "mayonnaise".

The compositions according to the invention can contain other ingredients, for example protective colloids, adhesives or sequestrants, as well as other active materials known to have pesticidal properties, especially insecticides or fungicides.

We claim:
1. A of of, the formula

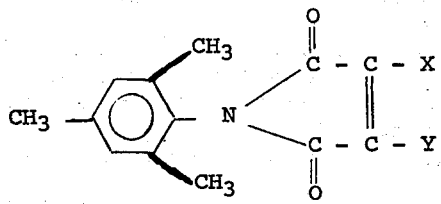

in which X and Y, which may be the same or different, represent hydrogen or a halogen atom.

2. Compounds as claimed in claim 1, wherein X and Y in the above formula are hydrogen or chlorine.

* * * * *

UNITED STATES PATENT OFFICE
CERTIFICATE OF CORRECTION

Patent No.  3,948,942                    Dated  April 6, 1976

Inventor(s)  Jean-Claude Debourge et al.

It is certified that error appears in the above-identified patent and that said Letters Patent are hereby corrected as shown below:

column 8, line 21, first line of Claim 1 should read:

A compound of the formula

Signed and Sealed this

Twentieth Day of July 1976

[SEAL]

Attest:

RUTH C. MASON  
Attesting Officer

C. MARSHALL DANN  
Commissioner of Patents and Trademarks